(12) United States Patent
Watermeier et al.

(10) Patent No.: US 6,793,662 B1
(45) Date of Patent: Sep. 21, 2004

(54) AMNIOTIC MEMBRANE PERFORATOR

(75) Inventors: David Wayne Watermeier, Knoxville, TN (US); Pamela Kay Hicks, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 10/623,399

(22) Filed: Jul. 18, 2003

(51) Int. Cl.[7] .......................... A61B 17/42; A61B 17/34
(52) U.S. Cl. ....................................... 606/125; 606/125
(58) Field of Search ................................ 606/125, 184, 606/185, 167, 171, 170

(56) References Cited

U.S. PATENT DOCUMENTS

| 3,533,411 A | | 10/1970 | McKnight et al. |
| 3,624,747 A | | 11/1971 | McKnight et al. |
| 5,846,250 A | * | 12/1998 | Parker, III ................... 606/125 |
| 5,968,055 A | * | 10/1999 | Dimitriu ..................... 606/125 |

OTHER PUBLICATIONS

Photo of Amniotic Membrane Perforator.

* cited by examiner

*Primary Examiner*—Vy Q. Bui
(74) *Attorney, Agent, or Firm*—Luedeka, Neely & Graham PC

(57) ABSTRACT

A one piece surgical device for perforating an amniotic membrane, the device including a elongate body defining a tip portion and an opposite handle potion, with the tip portion including a blunt end surface and a rearwardly projecting hook portion which is adjacent an upper edge of the body and the handle portion includes one or more raised surfaces located on the sides of the body closely adjacent the upper edge, wherein a user grasping the device may feel the raised surfaces to determine the orientation of the hook portion.

8 Claims, 3 Drawing Sheets

AMNIOTIC MEMBRANE PERFORATOR

FIELD OF THE INVENTION

This invention relates generally to surgical devices. More particularly, the invention relates to surgical devices for rupturing the amniotic membrane.

BACKGROUND AND SUMMARY OF THE INVENTION

In the birthing process, an obstetrician may perform a procedure to artificially rupture the amniotic membrane. Typically, the obstetrician will utilize a surgical tool that is inserted into the patient and includes a cutting or tearing surface to contact and rupture the amniotic membrane. An example of such devices and the manner of use of such devices is described in U.S. Pat. No. 3,533,411. Such prior devices desire improvement in their construction.

With regard to the foregoing, the present invention is directed to a surgical device for perforating an amniotic membrane.

In a preferred embodiment, the device includes an elongate body defining a tip portion and an opposite handle portion. The tip portion includes a blunt end surface and a rearwardly projecting hook portion which is adjacent an upper edge of the body. The handle portion includes one or more raised surfaces located on the sides of the body closely adjacent the upper edge. A user grasping the device may feel the raised surfaces to determine the orientation of the hook portion.

In another aspect, the surgical device includes a elongate body defining a tip portion and an opposite handle potion. The tip portion includes a blunt end surface and a rearwardly projecting hook portion which is adjacent an upper edge of the body and the handle portion. The handle portion includes a contoured rear end configured to facilitate one-handed use of the device. The contoured rear end includes a pair of enlarged lobes spaced apart from one another by a connecting segment, with the enlarged lobes and the connecting segment each having a thickness. The thickness of each of the enlarged lobes is greater than the thickness of the connecting segment.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
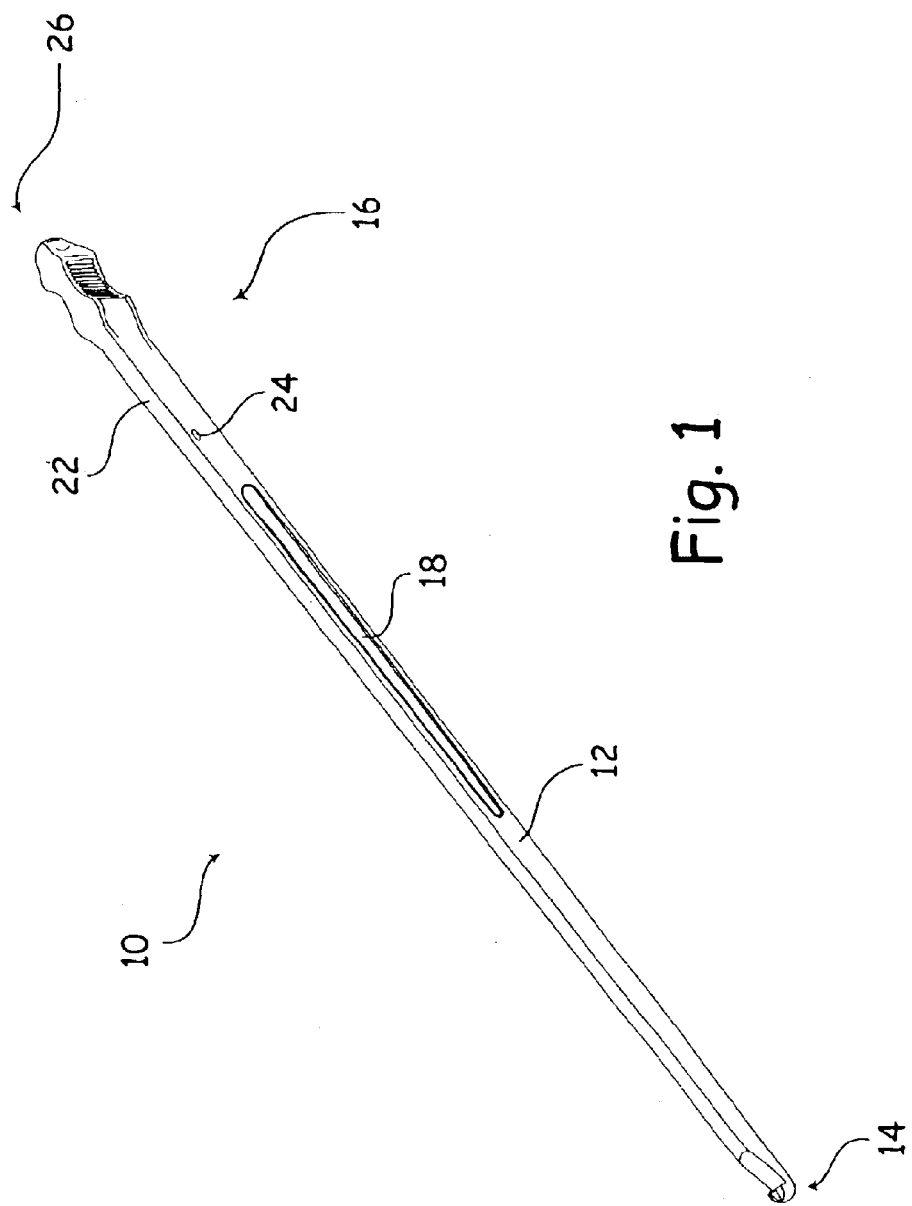
FIG. 1 is a perspective view of a surgical device according to a preferred embodiment of the invention.
Figure 2:
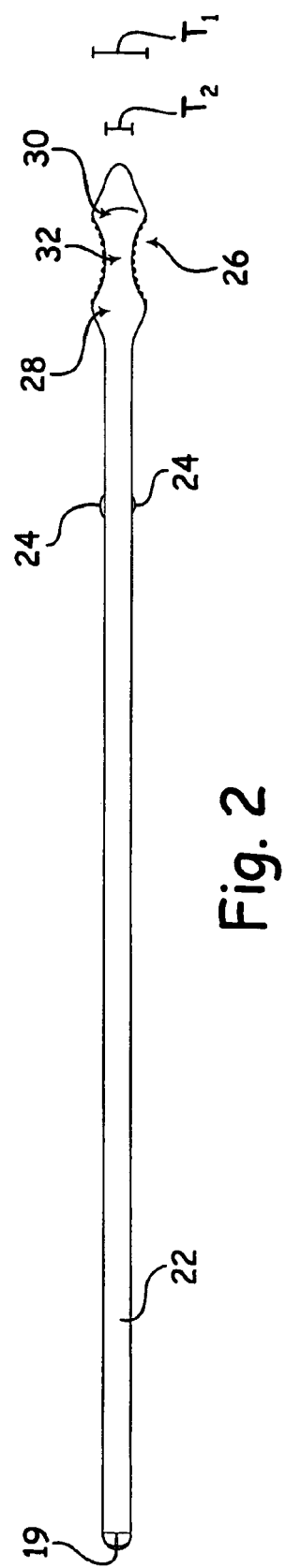
FIG. 2 is a top plan view of the surgical device of FIG. 1.
Figure 3:
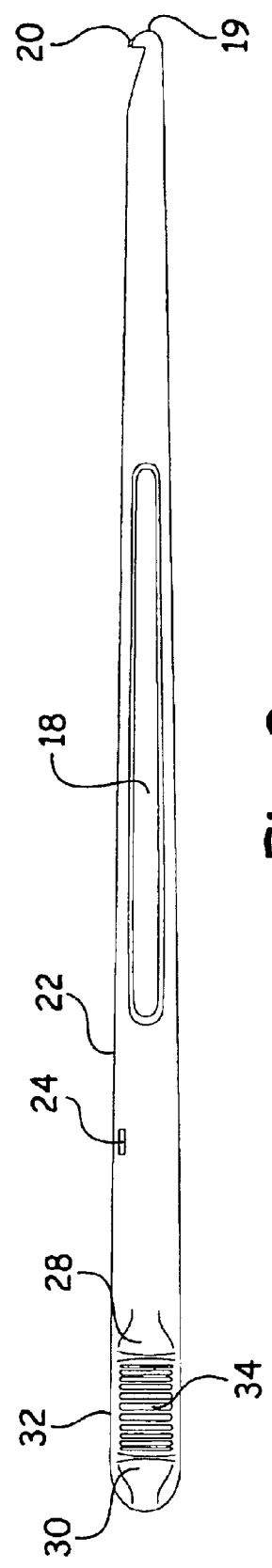
FIG. 3 is a side view of the surgical device of FIG. 1.

With reference to FIGS. 1–3, the invention relates to a surgical device 10 configured to be used to artificially rupture the amniotic membrane of a pregnant woman. In accordance with a preferred embodiment, the device 10 is preferably of one-piece molded plastic construction and includes an elongate body 12.

The body 12 is preferably tapered from a width of about ¼ inch at a smaller front or tip portion 14 to a width of about ½ inch at a larger rear or handle portion 16. The body 12 also preferably includes elongate recesses 18 on the opposite sides thereof, generally intermediate the tip portion 14 and the handle portion 16. The body 12 preferably has an overall length of from about 10 to 11 inches, with a substantially uniform thickness of about ⅛ inch, except. as described below in connection with the rear end 26 of the handle portion 16.

The tip portion 14 includes a blunt end surface 19 and a rearwardly projecting hook portion 20 which is adjacent an upper edge 22 of the body 12. The tip portion 14 is preferably configured substantially identical to the head end portion 14 described in U.S. Pat. No. 3,624,747 entitled SURGICAL INSTRUMENT FOR RUPTURING MEMBRANES, issued Nov. 30, 1971, and incorporated herein by reference in its entirety, and in particular FIGS. 2–5 and the associated description.

During use of the device 10, it is important that the user be able to position the hook portion 20 in a desired manner. Since the hook portion 20 is not visible during use, e.g., it is inserted into the patient, it may be difficult for the user to verify the orientation of the device 10 and the user may have to withdraw the device 10 to verify the manner in which the user has grasped the device 10. To facilitate desired orientation of the device 10, the handle portion 16 preferably includes one or more raised surfaces, such as bumps 24.

The bumps 24 are preferably located on the sides of the body 12 closely adjacent the upper edge 22. In use, it is generally desirable to orient the device 10 so that the hook 20, and hence the upper edge 20, is generally upwardly oriented. A user grasping the device 12 may feel the bumps 24 and by feel orient the device 10 so that the bumps 24 are upwardly oriented, ensuring that the upper end 22 and, hence the hook 20, are commonly oriented in the same general direction as the bumps 24. It is preferred to have at least two bumps positioned substantially across from one another, although a single bump may be used, or the bumps may be staggered.

The dimensions of the bumps 24 may be uniform or maybe different on each side, the only requirement being that the bumps be dimensioned and configured sufficient to enable a user to readily detect their presence by feel, even when wearing surgical gloves or the like. An example would be to have the bumps configured as elongate rounded protrusions having a length of from about 2 to about 2.5 millimeters, with the lengths of the bumps preferably being substantially parallel to the slope of the top edge 22. The bumps 24 are preferably raised from the side surface of the body 12 by a width of from about 0.5 to about 1 millimeter, with each bump 24 disposed about 2 millimeters from the top edge 22. However, it will be understood that the bumps may be otherwise configured and dimensions, so long as they may be readily detected by feel and located so as to enable a user to detect by tactile sense their orientation relative to a predetermined portion of the device, such as the upper edge 22 as previously described.

The handle portion 16 further includes a contoured rear end 26 configured to facilitate one-handed use of the device 10. In a preferred embodiment, the rear end 26 includes a pair of enlarged lobes 28 and 30 spaced apart from one another by a connecting segment 32. The center-to-center distance, e.g., the spacing of the lobes 28 and 30 is preferably from about ½ about ¾ inch.

The lobes 28 and 30 preferably have a maximum thickness T1 of from about ½ to about ¼ inch, and the maximum thickness T2 of the connecting segment 32 preferably corresponds to the thickness of the body 12, e.g., about ⅛ inch, such that the ratio of the thickness T1 of the enlarged lobes to the thickness T2 of the connecting segment is preferably from about 2 to about 4. The thickness of the lobes 28 and 30 preferably tapers toward the connecting segment 32, and toward the location where the lobe 28 joins the body 12 and toward the terminal free end of the portion 30 for comfort and aesthetics. The connecting segment 32 likewise includes a series of ribs or serrations 34 preferably running substantially parallel to the width or height of the segment 32 for facilitating gripping and for aesthetics.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A one piece surgical device for perforating an amniotic membrane, the device comprising a tapered elongate body having a substantially uniform, relatively narrow thickness defining a first side, a second side opposite the first side, a first edge, a second edge opposite the first edge, the body including a tip portion, a handle portion opposite the tip portion, elongate recesses on the first and second sides of the body between the tip portion and the handle portion, wherein the tip portion includes a blunt end surface on the first edge thereof and a hook portion projecting toward the handle portion on the second edge thereof, wherein the handle portion includes one or more raised orientation indicating surfaces located on the first and second sides of the handle portion closely adjacent the first edge, and wherein the handle portion is substantially devoid of raised orientation indicating surfaces adjacent the second edge.

2. The device of claim 1, wherein the raised surfaces comprise a first bump on the first side of the body and a second bump on the second side of the body.

3. The device of claim 1, wherein the handle portion further comprises a contoured rear end configured to facilitate one-handed use of the device and comprising a pair of enlarged lobes spaced apart from one another by a connecting segment, with the enlarged lobes and the connecting segment each having a thickness, with the thicknesses of the enlarged lobes each being greater than the thickness of the connecting segment and the thickness of the body, and wherein the enlarged lobes define tapered portions that are oriented substantially perpendicular to the elongate recesses in the elongate body.

4. A one piece surgical device for perforating an amniotic membrane, the device comprising a tapered elongate body having a substantially uniform, relatively narrow thickness defining a first side, a second side opposite the first side, a first edge, a second edge opposite the first edge, the body including a tip portion, a handle portion opposite the tip portion, and elongate recesses on the first and second sides of the body between the tip portion and the handle portion, wherein the tip portion includes a blunt end surface on the first edge thereof and a hook portion projecting toward the handle portion on the second edge thereof, wherein the handle portion includes a contoured rear end configured to facilitate one-handed use of the device and comprising a pair of enlarged lobes spaced apart from one another by a connecting segment, with the enlarged lobes and the connecting segment each having a thickness, wherein the thickness of the enlarged lobes is greater than the thickness of the connecting segment and the thickness of the body, and wherein the enlarged lobes define tapered portions that are oriented substantially perpendicular to the elongate recesses in the elongate body.

5. The device of claim 4, wherein a ratio of the thickness of each of the enlarged lobes to the thickness of the connecting segment is from about 2:1 to about 44:1.

6. A one piece surgical device for perforating an amniotic membrane, the device comprising a tapered elongate body having a substantially uniform thickness defining a first side, a second side opposite the first side, a first edge, a second edge opposite the first edge, the body including a tip portion, a handle portion opposite the tip portion, and elongate recesses on the first and second sides of the body between the tip portion and the handle portion, wherein the tip portion includes a blunt end surface on the first edge thereof and a hook portion projecting toward the handle portion on the second edge thereof, wherein the handle portion includes a first raised surface on the first side of the body closely adjacent the first edge and a second raised surface on the second side of the body closely adjacent the first edge for hook orientation determination by a user, and wherein the handle portion is substantially smooth adjacent the second edge.

7. The device of claim 6, wherein the raised surfaces comprise a first bump on the first side of the body and a second bump on the second side of the body.

8. The device of claim 7, wherein the handle portion further comprises a contoured rear end configured to facilitate one-handed use of the device and comprising a pair of enlarged lobes spaced apart from one another by a connecting segment, with the enlarged lobes and the connecting segment each having a thickness, with the thicknesses of the enlarged lobes each being greater than the thickness of the connecting segment and the thickness of the body, and wherein the enlarged lobes define tapered portions that are oriented substantially perpendicular to the elongate recesses in the elongate body.

* * * * *